US011498959B2

(12) United States Patent
Sharma

(10) Patent No.: US 11,498,959 B2
(45) Date of Patent: Nov. 15, 2022

(54) ANTI-CGRP ANTIBODY FORMULATION

(71) Applicant: Eli Lilly and Company, Indianapolis, IN (US)

(72) Inventor: Anant N Sharma, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 100 days.

(21) Appl. No.: 15/578,263

(22) PCT Filed: Jun. 8, 2016

(86) PCT No.: PCT/US2016/036407
§ 371 (c)(1),
(2) Date: Nov. 30, 2017

(87) PCT Pub. No.: WO2016/205037
PCT Pub. Date: Dec. 22, 2016

(65) Prior Publication Data
US 2018/0134772 A1   May 17, 2018

Related U.S. Application Data

(60) Provisional application No. 62/180,905, filed on Jun. 17, 2015.

(51) Int. Cl.
| | |
|---|---|
| *C07K 16/18* | (2006.01) |
| *A61K 39/395* | (2006.01) |
| *C07K 16/26* | (2006.01) |
| *A61P 25/00* | (2006.01) |
| *A61P 25/06* | (2006.01) |
| *A61K 39/00* | (2006.01) |

(52) U.S. Cl.
CPC ........ *C07K 16/18* (2013.01); *A61K 39/39591* (2013.01); *A61P 25/00* (2018.01); *A61P 25/06* (2018.01); *C07K 16/26* (2013.01); *A61K 2039/505* (2013.01); *A61K 2039/54* (2013.01); *A61K 2039/545* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 5,733,873 A | 3/1998 | Thomas et al. | |
| 6,627,187 B2 | 9/2003 | Yamazaki et al. | |
| 7,635,473 B2 | 12/2009 | Warne et al. | |
| 8,007,794 B2 | 8/2011 | Zeller et al. | |
| 8,211,649 B2 | 7/2012 | Migone et al. | |
| 8,349,321 B2 | 1/2013 | Burke et al. | |
| 8,623,367 B2 | 1/2014 | Momm et al. | |
| 2003/0138417 A1 | 7/2003 | Kaisheva et al. | |
| 2006/0210557 A1* | 9/2006 | Luisi .................... | A61K 47/183 424/133.1 |
| 2007/0086979 A1* | 4/2007 | Chevrier ................. | A61P 19/02 424/85.1 |
| 2008/0292625 A1* | 11/2008 | Schroeter ................ | A61P 25/00 424/133.1 |
| 2009/0110681 A1* | 4/2009 | Carroll .................... | A61P 17/00 424/139.1 |
| 2009/0148462 A1* | 6/2009 | Chevrier ................. | A61P 25/00 424/158.1 |
| 2010/0172862 A1* | 7/2010 | Correia .................... | A61P 37/02 424/85.2 |
| 2010/0260766 A1* | 10/2010 | Srivastava .......... | C07K 16/2863 424/142.1 |
| 2011/0130544 A1 | 6/2011 | Ram et al. | |
| 2011/0171217 A1* | 7/2011 | Badkar ................... | A61P 11/06 424/133.1 |
| 2011/0171241 A1* | 7/2011 | Dix ....................... | A61K 47/183 424/172.1 |
| 2011/0293605 A1* | 12/2011 | Sathish ................... | A61P 37/02 424/133.1 |
| 2011/0305711 A1* | 12/2011 | Allan ...................... | C07K 16/26 424/172.1 |
| 2012/0148576 A1* | 6/2012 | Sharma ................... | A61P 35/04 424/133.1 |
| 2013/0171194 A1* | 7/2013 | Khandke .......... | G01N 33/56911 424/250.1 |
| 2014/0170152 A1 | 7/2014 | Hsieh et al. | |

(Continued)

FOREIGN PATENT DOCUMENTS

| | | | |
|---|---|---|---|
| WO | 2003/039485 A2 | 5/2003 | |
| WO | 2006/081587 A2 | 8/2006 | |

(Continued)

OTHER PUBLICATIONS

Document from WIPO Examination of relation application for PCT/US2016/036407: "Written Opinion of the International Search Authority," Date of completion of this opinion as per Form PCT/ISA/210: Date of the actual completion of the International search Aug. 10, 2016, Date of mailing of the international search report: dated Aug. 31, 2016.
Walter Sarah et al.: "TEV-48125: a Review of a Monoclonal CGRP Antibody in Development for the Preventive Treatment of Migraine",Current Pain and Headache Reports, Current Science, US,vol. 19, No. 3, Mar. 10, 2015 (Mar. 10, 2015), pp. 1-6.
Dodick et al. Lancet Neurol; 13(9): 885-892 (2014).

*Primary Examiner* — Adam Weidner
(74) *Attorney, Agent, or Firm* — Robert L. Sharp; Parker D. McCrary

(57) ABSTRACT

Pharmaceutical formulations for anti-CGRP antibodies, and methods of using the same, are provided which are useful as treatment for migraines, episodic headaches, chronic headaches, chronic cluster headaches, and episodic cluster headaches.

32 Claims, 1 Drawing Sheet
Specification includes a Sequence Listing.

(56) References Cited

U.S. PATENT DOCUMENTS

2014/0227250 A1* 8/2014 Li .......................... A61P 11/06
                                                        424/133.1
2014/0234296 A1* 8/2014 Sharma ................ A61K 47/183
                                                        424/133.1

FOREIGN PATENT DOCUMENTS

| WO | 2006/083689 | A2 | 8/2006 |
| WO | 2006/096461 | A2 | 9/2006 |
| WO | 2008/071394 | A1 | 6/2008 |
| WO | 2008/086395 | A2 | 7/2008 |
| WO | 2010/077422 | A2 | 7/2010 |
| WO | 2011/156324 | A1 | 12/2011 |
| WO | 2014/114651 | A1 | 7/2014 |

* cited by examiner

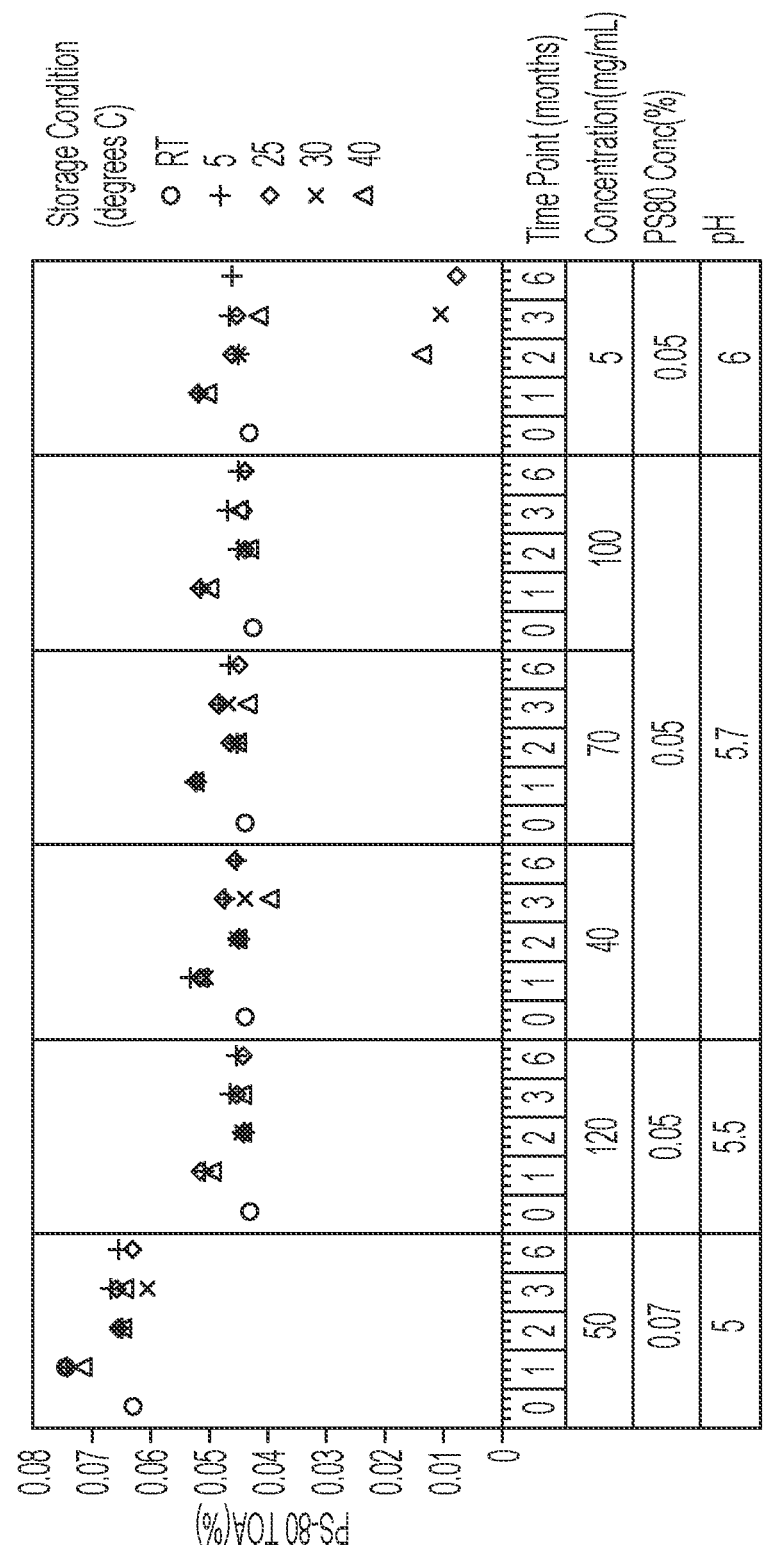

ANTI-CGRP ANTIBODY FORMULATION

The present invention is in the field of medicine. More specifically, the present invention relates to antibodies to calcitonin gene-related peptide (CGRP) and pharmaceutical formulations thereof. Additional aspects of the present invention relate to the use of such anti-CGRP antibodies and pharmaceutical formulations thereof for the treatment of patients suffering from CGRP-related disorders.

CGRP is a neuropeptide secreted by the nerves of the central and peripheral nervous systems and is implicated in pain pathways. The role of CGRP in headache and migraine has been established in the art and a number of clinical studies are currently evaluating the use of anti-CGRP antibodies for the treatment of headaches and migraine. (see, for example, Dodick et al. Lancet Neurol; 13(9): 885-892 (2014)).

Liquid pharmaceutical formulations for antibodies intended for human use require the chemical and physical stability of the antibody over its extended shelf life (e.g. WO06083689 and in WO06096491). Chemical instability of the antibody can result from a number of chemical reactions including deamidation, racemization, hydrolysis, oxidation, beta elimination and disulfide exchange. Physical instability can result from processes such as denaturation, aggregation, precipitation, and adsorption to surfaces. Instability of the antibody can result in the formation of a polypeptide by-product or derivatives having low activity, increased toxicity, and/or increased immunogenicity, which can pose concerns about the safety and efficacy of the antibody.

While the possible occurrence of protein instabilities is widely appreciated, it is difficult to predict particular instability issues for a particular protein. Applicants sought to formulate an anti-CGRP antibody (PCT/US2011/039381), wherein said antibody comprises a light chain variable region (LCVR) and a heavy chain variable region (HCVR), wherein the amino acid sequence of said LCVR is SEQ ID NO: 1 and the amino acid sequence of said HCVR is SEQ ID NO: 2. In formulating the anti-CGRP antibody for use in therapy, applicants discovered several factors that contributed to the instability of the antibody, such as photo degradation, polymer formation during freeze-thaw, and oxidation of polysorbate-80 (PS-80) in the formulation. Therefore, a stable pharmaceutical formulation was needed to overcome at least one or more of the observed issues.

BRIEF DESCRIPTION OF THE FIGURE

FIG. 1 shows the amount of polysorbate-80 remaining under a variety of formulation conditions.

Accordingly, the present invention provides a pharmaceutical formulation comprising an anti-CGRP antibody at a concentration of about 40 mg/mL to about 160 mg/mL, histidine buffer at a concentration of about 5 mM to about 20 mM, sodium chloride (NaCl) at a concentration of about 50 mM to about 200 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

In an alternative embodiment, the present invention provides a pharmaceutical formulation comprising an anti-CGRP antibody at a concentration of about 50 mg/mL to about 150 mg/mL, histidine buffer at a concentration of about 5 mM to about 20 mM, sodium chloride at a concentration of about 50 mM to about 200 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

In an alternative embodiment, the present invention provides a pharmaceutical formulation comprising an anti-CGRP antibody at a concentration of about 100 mg/mL to about 160 mg/mL, histidine buffer at a concentration of about 5 mM to about 20 mM, NaCl at a concentration of about 50 mM to about 200 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

A further embodiment of the present invention also provides a pharmaceutical formulation comprising an anti-CGRP antibody in a histidine buffer, NaCl, and PS-80, wherein the concentration of anti-CGRP antibody is selected from the group consisting of about 50 mg/mL, about 100 mg/mL, about 120 mg/mL or about 150 mg/mL, histidine buffer at a concentration of about 5 mM to about 20 mM, NaCl at a concentration of about 50 mM to about 200 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

Another embodiment of the present invention also provides a pharmaceutical formulation comprising an anti-CGRP antibody in a histidine buffer, NaCl, and PS-80, wherein the concentration of anti-CGRP antibody is selected from the group consisting of about 50 mg/mL, about 100 mg/mL, about 120 mg/mL or about 150 mg/mL, histidine buffer at a concentration of about 10 mM, NaCl at a concentration of about 50 mM to about 200 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

In another embodiment, the present invention also provides a pharmaceutical formulation comprising an anti-CGRP antibody in a histidine buffer, NaCl, and PS-80, wherein the concentration of anti-CGRP antibody is selected from the group consisting of about 50 mg/mL, about 100 mg/mL, about 120 mg/ml or about 150 mg/mL, histidine buffer at a concentration of about 10 mM, NaCl at a concentration of about 150 mM, PS-80 at a concentration of about 0.03% (w/v) to about 0.07% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

In another embodiment, the present invention also provides a pharmaceutical formulation comprising an anti-CGRP antibody in a histidine buffer, NaCl, and PS-80, wherein the concentration of anti-CGRP antibody is selected from the group consisting of about 50 mg/mL, about 100 mg/mL, about 120 mg/ml or about 150 mg/mL, histidine buffer at a concentration of about 10 mM, NaCl at a concentration of about 150 mM, PS-80 at a concentration of about 0.05% (w/v), and a pH at about 5.0 to about 6.5, wherein the anti-CGRP antibody comprises a light chain variable region (LCVR) and a heavy chain variable region (HCVR), the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

More particularly, the present invention provides for a pharmaceutical formulation comprising an anti-CGRP antibody at a concentration of about 120 mg/mL, histidine buffer at a concentration of about 10 mM, NaCl at a concentration of about 150 mM, PS-80 at a concentration of about 0.05% (w/v), and pH of about 5.8, wherein the anti-CGRP antibody comprises a LCVR and a HCVR, the amino acid sequence of LCVR given by SEQ ID NO: 1 and the amino acid sequence of HCVR given by SEQ ID NO: 2. Preferably, the pharmaceutical formulation comprises an anti-CGRP antibody with a light chain (LC) and a heavy chain (HC), the amino acid sequence of LC given by SEQ ID NO: 3 and the amino acid sequence of HC given by SEQ ID NO: 4. More preferably, the pharmaceutical formulation comprises an anti-CGRP antibody with two LCs and two HCs, the amino acid sequence of each LC given by SEQ ID NO: 3 and the amino acid sequence of each HC given by SEQ ID NO: 4.

In a further embodiment, the present invention provides a pharmaceutical formulation comprising an anti-CGRP antibody in a histidine buffer, wherein the concentration of the anti-CGRP antibody is about 40 mg/mL to about 160 mg/mL. Preferably, the concentration of the anti-CGRP antibody is about 50 mg/mL to about 150 mg/mL. More preferably, the concentration of the anti-CGRP antibody is about 50 mg/mL, about 100 mg/mL, about 120 mg/mL, or about 150 mg/mL. In particular embodiments the pharmaceutical formulation comprises an anti-CGRP antibody at a concentration of about 40 mg/mL to about 160 mg/mL in a histidine buffer, wherein the histidine buffer is at a concentration of about 5 mM to about 20 mM. Preferably, the histidine buffer is at a concentration of about 10 mM.

In another embodiment, the present invention provides a pharmaceutical formulation comprising an anti-CGRP antibody and NaCl, wherein the concentration of NaCl is about 50 mM to about 200 mM. Preferably, the concentration of NaCl is about 125 to about 175 mM. More preferably, the concentration of NaCl is about 150 mM. Even more preferably, the pharmaceutical formulation comprises an anti-CGRP antibody, histidine buffer at 10 mM, and NaCl, wherein the concentration of NaCl is about 50 mM to about 200 mM. Most preferably, the pharmaceutical formulation comprises an anti-CGRP antibody at a concentration in the range of about 40 mg/mL to about 160 mg/mL, histidine buffer at a concentration of about 10 mM, NaCl at a concentration of about 50 mM to about 200 mM, and a pH of about 5.8. Preferably, the NaCl is at a concentration of about 150 mM.

In another embodiment, the present invention provides a pharmaceutical formulation comprising an anti-CGRP antibody and PS-80, wherein the concentration of PS-80 is about 0.03% (w/v) to about 0.07% (w/v). Preferably the concentration of PS-80 in the pharmaceutical formulation is about 0.05% (w/v). In a preferred embodiment, the pharmaceutical formulation comprises an anti-CGRP antibody at a concentration in the range of about 40 mg/mL to about 160 mg/mL, and PS-80 at a concentration of about 0.03% (w/v) to about 0.07% (w/v). More preferably, the pharmaceutical formulation comprises an anti-CGRP antibody at a concentration in the range of about 40 mg/mL to about 160 mg/mL, histidine buffer at a concentration of about 5 mM to 20 mM, and of PS-80 is about 0.05% (w/v). Even more preferably, the pharmaceutical formulation comprises an anti-CGRP antibody at a concentration in the range of about 40 mg/mL to about 160 mg/mL, NaCl at a concentration of about 50 mM to about 200 mM, and PS-80 at a concentration of about 0.05% (w/v). Most preferably, the pharmaceutical formulation comprises an anti-CGRP antibody at a concentration in the range of about 100 mg/mL to about 150 mg/mL, histidine buffer at a concentration of about 125 mM to about 175 mM, PS-80 at a concentration of about 0.05% (w/v) and a pH of about 5.8.

The present invention also provides a method of treating or preventing a condition related to elevated levels of CGRP, preferably headaches and/or migraines comprising administering to a patient in need thereof a therapeutically effective amount of a pharmaceutical formulation of the present invention. Some embodiments of the present invention provide a method of treating or preventing migraine, episodic headache, chronic headache, chronic cluster headaches, and/or episodic cluster headaches comprising administering to a patient in need thereof a therapeutically effective amount of a pharmaceutical formulation of the present invention. According to some embodiments, a method of treating or preventing chronic and episodic cluster headaches is provided comprising administering to a patient in need thereof a dose of 300 mg of an anti-CGRP antibody. Further embodiments provide a method of treating or preventing chronic and episodic cluster headaches administering to a patient in need thereof a dose of 360 mg of an anti-CGRP antibody. In other embodiments, the present invention provides a method of treating or preventing chronic and episodic migraines comprising administering to a patient in need thereof a dose of 120 mg of an anti-CGRP antibody. Further embodiments provide a method of treating or preventing chronic and episodic migraine comprising administering to a patient in need thereof a dose of 240 mg of an anti-CGRP antibody. Another embodiment provides a provide a method of treating or preventing chronic and episodic migraine comprising administering to a patient in need thereof an initial loading dose of 240 mg of an anti-CGRP antibody followed by a monthly maintenance dose of 120 mg of an anti-CGRP antibody. Preferably, the dose is administered at weekly, semi-monthly, monthly or quarterly intervals. More preferably, the administration is monthly.

In another embodiment, the present invention also provides a method to treat or prevent cluster headache in a patient in need by administering a monthly subcutaneous dose of 300 mg of an anti-CGRP antibody, wherein the anti-CGRP antibody binds to an epitope comprising amino acids VTHRLAGLLSR of SEQ ID NO: 7. In a further embodiment, the present invention provides a method to treat or prevent episodic migraine in a patient in need by administering a monthly subcutaneous dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2. Preferably, the anti-CGRP antibody is in a pharmaceutical formulation comprising about 10 mM histidine buffer, about 150 mM NaCl, about 0.05% PS-80, and a pH of about 5.8. In another embodiment, the present invention also provides a method to treat or prevent cluster headache in a patient in need by administering a monthly subcutaneous dose of 300 mg of an anti-CGRP antibody, wherein the anti-CGRP antibody comprises a LC given by the amino acid sequence of SEQ ID NO: 3 and a HC given by the amino acid of SEQ ID NO: 4. Preferably, the anti-CGRP antibody is in a pharmaceutical formulation comprising about 10 mM histidine buffer, about 150 mM NaCl, about 0.05% PS-80 and a pH of about 5.8.

In another embodiment, the present invention also provides a method to treat or prevent cluster headache in a patient in need thereof by administering a monthly dose of 300 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a histidine buffer. In a particular embodiment, the anti-CGRP antibody is in a pharmaceutical composition comprising a histidine buffer at a pH of about 5.5-6.1. In another particular embodiment, the anti-CGRP antibody is in a pharmaceutical composition comprising about 5 mM to about 20 mM histidine buffer. Preferably the pharmaceutical composition has a pH of about 5.7-6.0. More preferably, the pharmaceutical composition has a pH of about 5.8.

In another particular embodiment, the present invention also provides a method to treat or prevent cluster headache in a patient in need thereof by administering a monthly dose of 300 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, NaCl, and a surfactant. Preferably the anti-CGRP antibody is in a pharmaceutical composition comprising a buffer, about 50 mM to about 200 mM of NaCl, and a surfactant. More preferably, the anti-CGRP antibody is in a pharmaceutical composition at a pH of about 5.7-6.0. Most preferably, the anti-CGRP antibody is in a pharmaceutical composition at a pH of about 5.8.

In another particular embodiment, the present invention also provides a method to treat or prevent cluster headache in a patient in need thereof by administering a monthly dose of 300 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, salt, and PS-80 as a surfactant. Preferably the anti-CGRP antibody is in a pharmaceutical composition comprising a buffer, salt, and about 0.03% (w/v) to about 0.07% (w/v) PS-80. More preferably, the anti-CGRP antibody is in a pharmaceutical composition at a pH of about 5.7-6.0. Most preferably, the anti-CGRP antibody is in a pharmaceutical composition at a pH of about 5.8.

In a further embodiment, the present invention provides a method to treat or prevent episodic migraine in a patient in need by administering a monthly subcutaneous dose of 120 mg of an anti-CGRP antibody, wherein the anti-CGRP antibody binds to an epitope comprising amino acids VTHRLAGLLSR of SEQ ID NO: 7. In a further embodiment, the present invention provides a method to treat or prevent episodic migraine in a patient in need by administering a monthly subcutaneous dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2. Preferably, the anti-CGRP antibody is in a pharmaceutical formulation comprising about 10 mM histidine buffer, about 150 mM NaCl, about 0.05% PS-80, and a pH of about 5.8. In a further embodiment, the present invention provides a method to treat or prevent episodic migraine in a patient in need by administering a monthly subcutaneous dose of 120 mg of an anti-CGRP antibody, wherein the anti-CGRP antibody comprises a LC given by the amino acid sequence of SEQ ID NO: 3 and a HC given by the amino acid of SEQ ID NO: 4. Preferably, the anti-CGRP antibody is in a pharmaceutical formulation comprising about 10 mM histidine buffer, about 150 mM NaCl, about 0.05% PS-80 and a pH of about 5.8.

In another embodiment the present invention provides a method to treat or prevent episodic migraine in a patient in need thereof by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a histidine buffer. In a particular embodiment, the anti-CGRP antibody is in a pharmaceutical composition comprising a histidine buffer at a pH of about 5.5-6.1. In another particular embodiment, the anti-CGRP antibody is in a pharmaceutical composition comprising about 5 mM to about 20 mM histidine buffer. Preferably the pharmaceutical composition has a pH of about 5.7-6.0. More preferably, the pharmaceutical composition has a pH of about 5.8.

In another particular embodiment, the present invention provides a method to treat or prevent episodic migraine in a patient in need thereof by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, NaCl, and a surfactant. Preferably the anti-CGRP antibody is in a pharmaceutical composition comprising a buffer, about 50 mM to about 200 mM of NaCl, and a surfactant. More preferably, the anti-CGRP antibody is in a pharmaceutical composition at a pH of about 5.7-6.0. Most preferably, the anti-CGRP antibody is in a pharmaceutical composition at a pH of about 5.8.

In another particular embodiment the present invention provides a method to treat or prevent episodic migraine in a patient in need by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, salt and PS-80 as a surfactant. Preferably the anti-CGRP antibody is in a pharmaceutical composition comprising a buffer, salt, and about 0.03% (w/v) to about 0.07% (w/v) PS-80. More preferably, the anti-CGRP antibody is in a pharmaceutical composition at a pH of about 5.7-6.0. Most preferably, the anti-CGRP antibody is in a pharmaceutical composition at a pH of about 5.8.

In another embodiment the present invention provides a method to treat or prevent chronic migraine in a patient in need thereof by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a histidine buffer. In a particular embodiment, the anti-CGRP antibody is in a pharmaceutical composition comprising a histidine buffer at a pH of about 5.5-6.1. In another particular embodiment, the anti-CGRP antibody is in a pharmaceutical composition comprising about 5 mM to about 20 mM histidine buffer. Preferably the pharmaceutical composition has a pH of about 5.7-6.0. More preferably, the pharmaceutical composition has a pH of about 5.8.

In another particular embodiment, the present invention provides a method to treat or prevent chronic migraine in a patient in need by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, NaCl, and a surfactant. Preferably the anti-CGRP antibody is in a pharmaceutical composition comprising a buffer, about 50 mM to about 200 mM of NaCl, and a surfactant. More preferably, the anti-CGRP antibody is in a pharmaceutical composition at a pH of about 5.7-6.0. Most preferably, the anti-CGRP antibody is in a pharmaceutical composition at a pH of about 5.8.

In another particular embodiment the present invention provides a method to treat or prevent chronic migraine in a patient in need by administering a monthly dose of 120 mg of an anti-CGRP antibody, wherein the anti-CGRP antibody comprises a LCVR given by the amino acid sequence of SEQ ID NO: 1 and a HCVR given by the amino acid of SEQ ID NO: 2, and wherein the anti-CGRP antibody is in a pharmaceutical composition comprising a buffer, salt and PS-80 as a surfactant. Preferably the anti-CGRP antibody is in a pharmaceutical composition comprising a buffer, salt, and about 0.03% (w/v) to about 0.07% (w/v) PS-80. More preferably, the anti-CGRP antibody is in a pharmaceutical composition at a pH of about 5.7-6.0. Most preferably, the anti-CGRP antibody is in a pharmaceutical composition at a pH of about 5.8. The present invention also provides a pharmaceutical formulation for use in therapy, preferably for use in the treatment or prevention of migraines and/or headaches. In particular embodiments, the present invention provides a pharmaceutical formulation for use in the treatment or prevention of at least one or more of the following conditions: episodic migraine, chronic migraine, episodic headaches, chronic headaches, chronic cluster headaches, and/or episodic cluster headaches. Preferably, the dose of anti-CGRP antibody that is administered to a patient is 120 mg or 240 mg for episodic and/or chronic migraine and 300 mg or 360 mg for episodic and/or chronic cluster headaches. Moreover, the present invention provides for a use of a pharmaceutical formulation of the present invention in the manufacture of a medicament for the treatment or prevention of migraine and/or headache. In particular, the present invention provides for a use of a pharmaceutical formulation in the manufacture of a medicament for the treatment of at least one or more of the following conditions: episodic migraine, chronic migraine, episodic headache, chronic headache, chronic cluster headache, and/or episodic cluster headache.

As used herein, the term "patient" refers to a human. In some embodiments, a patient is a human who has been diagnosed as having a condition or disorder for which treatment or administration with a pharmaceutical formulation of the present invention is indicated. In some embodiments, a patient is a human that is characterized as being at risk of a condition or disorder for which treatment or administration with a pharmaceutical formulation of the present invention is indicated.

As used herein, the term "treating" (or "treat" or "treatment") refers to processes involving a slowing, interrupting, arresting, controlling, stopping, reducing, or reversing the progression or severity of a symptom, disorder, condition, or disease, but does not necessarily involve a total elimination of all disease-related symptoms, conditions, or disorders associated with CGRP activity. As used herein, the term "prevention" (or "prevent" or "preventing") refers to precluding, averting, obviating, forestalling, reducing the incidence of, stopping, or hindering the symptoms of a disease, disorder and/or condition. Prevention includes administration to a subject who does not exhibit symptoms of a disease, disorder, and/or condition at the time of administration.

As used herein, the term "therapeutically effective amount" refers to the amount or dose of an anti-CGRP antibody in a pharmaceutical formulation of the present invention, which upon single or multiple dose administration to the patient, provides the desired pharmacological effect in the patient. A dose can include a higher initial loading dose, followed by a lower dose. A "dose" refers to a predetermined quantity of a therapeutic drug calculated to produce the desired therapeutic effect in a patient. A therapeutically effective amount can be determined by the attending diagnostician, as one skilled in the art, by considering a number of factors such as the patient's size, age, and general health, the specific disease or surgical procedure involved, the degree or severity of the disease or malady, the response of the individual patient, the mode of administration, the bioavailability characteristics of the preparation administered, the dose regimen selected, and the use of any concomitant medications.

As used herein, the term "month" or derivations thereof, refers to a time period that includes 28 to 31 consecutive days. The term "about" as used herein, means in reasonable vicinity of the stated numerical value, such as plus or minus 10% of the stated numerical value.

The general structure of an "antibody" is known in the art. Anti-CGRP antibodies are disclosed in WO2011/156324. As used herein, a "drug substance" ("DS") is a formulation that comprises an antibody, buffer (e.g. histidine), excipient (e.g. NaCl), and surfactant (e.g. PS-80), and is within a certain pH range or at a specified pH. A "drug product" ("DP") is a formulation comprising a buffer, excipient, surfactant, and antibody, wherein the antibody in the DP may be at a lower concentration than the antibody concentration in the DS.

The pharmaceutical formulations of the present invention are in the liquid dosage form of a solution. Administration of the pharmaceutical formulations of the present invention may be via parenteral administration. Parenteral administration, as used herein, may include injection of a dosage form into the body by a sterile syringe or some other mechanical device such as an infusion pump. Parenteral routes can include intravenous, intramuscular, subcutaneous, and intraperitoneal routes of administration. Subcutaneous administration is a preferred route. The pharmaceutical formulations of the present invention are intended for pharmaceutical use in a human.

The invention is further illustrated by the following examples which should not be construed as limiting.

EXAMPLES

Production of Antibodies

Antibodies of the invention can be made and purified as follows. An appropriate host cell, such as CHO, is either transiently or stably transfected with an expression system for secreting antibodies using an optimal predetermined HC:LC vector ratio or a single vector system encoding both LC and both HC, such as each LC being SEQ ID NO: 3 and each HC being SEQ ID NO: 4. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient. Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. in the formulation matrix of the invention or may be lyophilized. The amino acid and nucleic acid sequences for the exemplified antibody are provided below.

Manufacture of an Anti-CGRP Pharmaceutical Formulation

The manufacturing process for an anti-CGRP antibody pharmaceutical formulation of the present invention includes compounding of the buffer excipient composition, and adding the anti-CGRP antibody drug substance (DS).

The buffer excipient composition consists of L-Histidine, L-Histidine Hydrochloride Monohydrate, NaCl, PS-80, and water (Table 1). The anti-CGRP antibody comprises a light chain of SEQ ID NO: 3, and a heavy chain of SEQ ID NO: 4.

TABLE 1

Buffer excipient composition

| Component | Quantity (mg/mL) | Final Concentration |
| --- | --- | --- |
| L-Histidine | 0.478 | 10 mM |
| L-Histidine Hydrochloride Monohydrate | 1.45 | |
| NaCl | 8.76 | 150 mM |
| PS-80 | 0.50 | 0.05% (w/v)* |
| Water for Injection | q.s. to 1 mL | |

*weight per volume

The buffer excipient composition is prepared and filtered. An appropriate quantity of water at a temperature not more than 25° C. is weighed into a tared empty vessel of appropriate size. The appropriate quantities of L-Histidine, L-Histidine Hydrochloride Monohydrate and NaCl are added and mixed. PS-80 is weighed out in a glass container and an appropriate quantity of water is added into the glass container to give the indicated final concentration, and the solution is mixed. The PS-80 solution is added to the other excipients, the solution is mixed, and the solution is prepared to have a pH and osmolality adjusted to within 5.8±0.3 and 254-344 mOsm/Kg, respectively. The buffer excipient composition is passed through a filter for bioburden reduction.

The anti-CGRP antibody DS is prepared by expressing the antibody in cells, purifying, concentrating, and freezing the antibody in solution in 10 mM histidine buffer, 150 mM NaCl, 0.05% PS-80, and pH of about 5.8. The DS solution is stored at −70° C. The frozen DS is equilibrated to a temperature of 20±5° C. and mixed with an appropriate amount of the buffer excipient solution to achieve the intermediate antibody DP concentration. The pH of the solution is checked to be within 5.8±0.3.

The solution is mixed and a sample is taken for an in-process UV assay to determine the antibody DP concentration. An appropriate quantity of the buffer excipient solution is added to reach the final target batch weight. After mixing, the pH of the solution is checked to be within 5.8±0.3. The antibody DP solution is passed through a filter for bioburden reduction prior to sterile filtration and filling into vials or syringes. The final concentration of the antibody DP can be between about 40 mg/mL to about 160 mg/mL.

Photo Stability

Light can influence the active molecule in a drug formulation, as well as the final product or package resulting in photodegradation that may result in the loss of potency of the product. The effect of light on anti-CGRP antibody formulated in citrate buffer or histidine buffer at pH 5.8 in glass prefilled syringes is evaluated by size exclusion chromatography (SEC). The light exposure levels are approximately 20% of ICH Q1B for visible light and 10% for the UV light.

Anti-CGRP antibody, at approximately 165 mg/mL (in 10 mM Histidine, 150 mM NaCl, pH 6.0), is divided into two aliquots. One aliquot is dialyzed into 10 mM histidine, 150 mM NaCl, pH 5.8 buffer, and the other aliquot is dialyzed into 10 mM citrate, 150 mM NaCl, pH 5.8 buffer. Following dialysis, the antibody is diluted with the appropriate buffer (histidine or citrate) to 50 mg/mL or to 120 mg/mL. PS-80 is added to each formulation to a final concentration of 0.05%. The formulations are filtered through a 0.22 μm sterilizing grade PVDF filter and filled into glass prefilled syringes. Eight syringes per formulation for size exclusion chromatography (SEC) analysis are utilized. Syringes are placed in light chambers for exposure to either ultraviolet (UV), visible or both UV and visible light. Syringes in an opaque box are also included as "dark" controls. The temperature is constant at 20° C. Total polymer is measured by SEC. The results are summarized in Table 2.

TABLE 2

Comparison of percent total polymer between histidine and citrate buffer

| DP Concentration and Light Condition | Histidine Buffer Total Polymer (%) | Citrate Buffer Total Polymer (%) |
|---|---|---|
| 50 mg/mL Dark | 1.44 | 1.70 |
| 50 mg/mL UV | 1.63 | 2.06 |
| 50 mg/mL VIS | 1.88 | 2.60 |
| 50 mg/mL UV/VIS | 2.33 | 3.47 |
| 120 mg/mL Dark | 1.54 | 1.98 |
| 120 mg/mL UV | 2.18 | 2.89 |
| 120 mg/mL VIS | 2.38 | 3.66 |
| 120 mg/mL UV/VIS | 2.86 | 4.20 |

Under conditions essentially as described above, the results provided in Table 2 demonstrate that the percent total polymer in histidine buffer were lower than that observed with citrate buffer. These data demonstrate that the formulations comprising the histidine buffer provide for better stability following exposure to light compared to formulations comprising citrate.

Excipient Compatibility Study

Stability of anti-CGRP antibody pharmaceutical formulations is evaluated in an excipient compatibility study. The formulations, at pH 6.0, comprise 120 mg/mL anti-CGRP antibody, 0.04% PS-80, either 10 mM or 20 mM histidine buffer, and either 150 mM NaCl, 5% mannitol, or a combination of 100 mM NaCl and 1.5% mannitol. Formulations are prepared by dialysis, and stored in HDPE containers at indicated temperatures, and are protected from light. Total polymer is determined by SEC at the beginning of the study, at 1 month, and at 2 months.

TABLE 3

Comparison of percent total polymer between mannitol, NaCl, and a combination of mannitol and NaCl.

| Formulation | Time points (months) | Total Polymer (%), 5° C. | Total Polymer (%), 25° C. | Total Polymer (%), 40° C. |
|---|---|---|---|---|
| 10 mM Histidine, 150 mM NaCl | 0 | 1.53 | 1.53 | 1.53 |
| | 1 | 1.68 | 2.02 | 2.43 |
| | 2 | 1.74 | 2.30 | 3.13 |
| 20 mM Histidine, 5% Mannitol | 0 | 1.98 | 1.98 | 1.98 |
| | 1 | 2.09 | 2.37 | 2.60 |
| | 2 | 2.17 | 2.71 | 3.22 |
| 10 mM Histidine, 100 mM NaCl, 1.5% Mannitol | 0 | 1.44 | 1.44 | 1.44 |
| | 1 | 1.59 | 1.74 | 2.11 |
| | 2 | 1.56 | 2.09 | 2.84 |

Under conditions essentially as described above, the percent total polymer in the formulation comprising 5% mannitol was higher compared to the percent total polymer for the formulation comprising 150 mM NaCl, or the formulation comprising 100 mM NaCl and 1.5% mannitol. The addition of NaCl and/or a combination of NaCl and mannitol is shown to positively affect the stability of the protein.

Stability Following Freeze-Thaw Freezing is a common processing step used to maintain stability and quality of a protein during development and production, and may allow for a longer shelf life. However, freezing can induce complex physical and chemical changes in the solvent/solute conditions, resulting in denaturation of proteins with the possibility of generation of aggregates over time. The stability of pharmaceutical formulations in histidine buffer following freeze-thaw (FT) is determined by SEC. Eight different formulations are prepared and stored in HDPE containers. Each formulation is at pH 6.0, comprises 0.02% PS-80.10 mM histidine, and either 150, 120, 100, or 20 mg/mL anti-CGRP antibody DP, and either 5% mannitol, 150 mM NaCl, or 1.5% mannitol and 100 mM NaCl.

Respective formulations in HDPE containers undergo three freeze-thaw cycles. For one cycle, each formulation is frozen at −70° C. and thawed at room temperature. Respective formulations in HDPE containers undergo a slow freeze-thaw in a lyophilizer chamber. Controls are stored at 5° C. for the duration of the study. Following the third cycle or following the slow freeze-thaw, percent total polymer is assessed by SEC.

TABLE 4

Comparison of percent total polymer between mannitol, NaCl, and a combination of mannitol and NaCl.

| | Total Polymer (%) | | | | | | | |
|---|---|---|---|---|---|---|---|---|
| | 5% Mannitol | | 150 mM NaCl | | | 1.5% Mannitol, 100 mM NaCl | | |
| Stress | 120 mg/ml DP | 20 mg/ml DP | 150 mg/mL DP | 100 mg/mL DP | 20 mg/mL DP | 150 mg/mL DP | 100 mg/mL DP | 20 mg/mL DP |
| Control | 1.7 | 2.2 | 1.64 | 1.65 | 1.19 | 1.45 | 1.6 | 1.2 |
| FT cycle 1 | 1.8 | 2.8 | 1.58 | 1.65 | 1.71 | 1.57 | 1.51 | 1.28 |
| FT cycle 2 | N.D. | N.D. | 1.62 | 1.66 | 2.32 | 1.54 | 1.51 | 1.33 |
| FT cycle 3 | 1.8 | 5.1 | 1.6 | 1.61 | 3.15 | 1.51 | 1.5 | 1.29 |
| Slow FT | 1.9 | 11.6 | 1.72 | 1.71 | 1.91 | 1.52 | 1.48 | N.D. |

N.D.: Not determined

Under conditions described above, the percent total polymer in the formulation comprising 5% mannitol and 20 mg/mL DP was increased in FT cycle 3 and in the slow FT, compared to the percent total polymer in all other formulations. The percent polymer was also increased in the formulation comprising 20 mg/mL DP and 150 mM NaCl. NaCl and/or a combination of NaCl and mannitol, together with concentrations of antibody greater than 20 mg/mL in the formulation are shown to have a stabilizing effect on the protein following freeze-thaw.

Capillary Shear Device

The capillary shear device (CSD) is a high shear force simulating stress device that uses a peristaltic pump and a capillary tube to study physical stress on a formulated DP. A CSD is used to evaluate shear force physical stress of pharmaceutical formulations of the present invention, wherein said formulations comprise 10 mM histidine, 150 mM NaCl, anti-CGRP antibody at a concentration of 5 mg/mL, 40 mg/mL, or 120 mg/mL, varying concentrations of PS-80, and pH of 6.0.

Anti-CGRP antibody DP is pumped through a 0.5 mm inner diameter stainless steel capillary tube, with or without air, at a rate of approximately 3.3 mL/sec using a peristaltic pump. This pump rate results in a shear value of approximately 105 sec$^{-1}$. Calculated energy dissipation is approximately 105 W/Kg. Controls do not undergo pumping.

Three different capillary shear device set-ups are utilized in this study. Stainless steel and PTFE capillary tubes are chosen because these materials are commonly used in manufacturing. Stainless steel capillary tubes without air in the system or PTFE capillary tubes without air in the system both represent a nominal stress condition. Nominal stress will be encountered when the solution is pumped using a peristaltic pump through a filling needle. Stainless steel capillary tubes with air entrapment in the system represent a high stress condition because the protein can unfold relatively easy in the air-liquid interface. Total polymer is determined by SEC, and particulate matter is determined by high accuracy particle counter (HIAC). SEC data are shown in Table 5, and HIAC data are shown in Table 6.

TABLE 5

Percent Total Polymer—SEC

| % PS-80 | Control | Stainless Steel | Stainless Steel with Air |
|---|---|---|---|
| 5 mg/ml Antibody | | | |
| 0 | 0.89 | 0.91 | 1.65 |
| 0.005 | 1.04 | 1.03 | 1.63 |
| 0.02 | 1.06 | 1.06 | 1.13 |
| 0.03 | 1.09 | 1.06 | 1.12 |
| 0.05 | 1.17 | 1.19 | 1.23 |
| 40 mg/ml Antibody | | | |
| 0 | 1.23 | 1.23 | 2.49 |
| 0.005 | 1.24 | 1.24 | 1.35 |
| 0.02 | 1.30 | 1.25 | 1.47 |
| 0.03 | 1.31 | 1.30 | 1.52 |
| 0.05 | 1.31 | 1.38 | 1.50 |
| 120 mg/ml Antibody | | | |
| 0 | 1.58 | 1.61 | 1.86 |
| 0.005 | 1.48 | 1.66 | 1.66 |
| 0.02 | 1.48 | 1.68 | 1.68 |
| 0.03 | 1.49 | 1.65 | 1.59 |
| 0.05 | 1.51 | 1.75 | 1.65 |

TABLE 6

Particulate Matter—HIAC
40 mg/mL anti-CGRP Antibody

| % PS-80 | Tubing Type | Particle Size (2 μm) | Particle Size (5 μm) | Particle Size (10 μm) | Particle Size (25 μm) |
|---|---|---|---|---|---|
| 0 | Control | 296 | 104 | 21 | 4 |
| 0.005 | Control | 53 | 26 | 11 | 6 |
| 0.02 | Control | 53 | 21 | 8 | 0 |
| 0.03 | Control | 57 | 19 | 6 | 1 |
| 0.05 | Control | 78 | 24 | 5 | 0 |
| 0 | Stainless Steel | 20284 | 1882 | 201 | 3 |
| 0.005 | Stainless Steel | 2612 | 501 | 94 | 4 |
| 0.02 | Stainless Steel | 1660 | 401 | 79 | 4 |
| 0.03 | Stainless Steel | 501 | 144 | 37 | 2 |
| 0.05 | Stainless Steel | 650 | 178 | 47 | 0 |
| 0 | Stainless Steel w/ Air | 62009 | 45330 | 24688 | 3683 |
| 0.005 | Stainless Steel w/ Air | 1225 | 344 | 162 | 2 |
| 0.02 | Stainless Steel w/ Air | 2993 | 803 | 178 | 4 |
| 0.03 | Stainless Steel w/ Air | 3959 | 946 | 135 | 0 |

TABLE 6-continued

Particulate Matter—HIAC
40 mg/mL anti-CGRP Antibody

| % PS-80 | Tubing Type | Particle Size (2 μm) | Particle Size (5 μm) | Particle Size (10 μm) | Particle Size (25 μm) |
|---|---|---|---|---|---|
| 0.05 | Stainless Steel w/ Air | 972 | 285 | 73 | 4 |

The SEC data in Table 5 show that under conditions essentially described above, the addition of PS-80 to the stainless steel with air groups (high stress conditions) led to a reduction in the total polymer.

Compared to formulations lacking PS-80, the addition of 0.005%, 0.02%, 0.03%, or 0.05% of PS-80 led to a reduction in particle formation in most of the groups as determined by HIAC (Table 6). These studies demonstrate that the addition of PS-80 to the solution reduces the particulate matter present in the anti-CGRP antibody formulation.

PS-80 Oxidation

Formulations at pH 6.0 comprising the anti-CGRP antibody (120 mg/ml), 10 mM histidine, 150 mM NaCl, and 0.05% PS-80 are used to determine PS-80 oxidation at various temperatures and time-points. Respective formulations are filled into vials or glass prefilled syringes and placed in chambers at room temperature (at the beginning of the study), 5° C., 25° C., or 40° C. The corresponding buffer (10 mM histidine, 150 mM NaCl, 0.05% PS-80, pH 6.0) without the antibody is used as a control. PS-80 hydrolysis method is used to determine percent PS-80. Amount of free oleic acid and amount of total oleic acid are determined. PS-80 hydrolysis results in total oleic acid (TOA), and TOA is measured by high-performance liquid chromatography (HPLC). To obtain the percent of intact PS-80, free oleic acid is subtracted from the total oleic acid.

TABLE 7

Percent PS-80 in formulations at various time-points and temperatures

| PS-80 % | Time (months) | Temperature | Control (%) | DP (%) |
|---|---|---|---|---|
| 14 mL Vial | 0 | RT | 0.051 | 0.052 |
| | 1 | 5° C. | 0.052 | 0.05 |
| | | 25° C. | 0.054 | 0.051 |
| | | 40° C. | 0.051 | 0.052 |
| | 3 | 5 C. | 0.052 | 0.052 |
| | | 25 C. | 0.054 | 0.051 |
| | 6 | 5 C. | 0.054 | 0.051 |
| | | 25 C. | 0.047 | 0.05 |
| 2.25 mL Syringe | 1 | 5 C. | 0.051 | 0.05 |
| | | 25 C. | 0.048 | 0.051 |
| | | 40 C. | 0.029 | 0.05 |
| | 3 | 5 C. | 0.052 | 0.051 |
| | | 25 C. | 0.008 | 0.05 |
| | 6 | 5 C. | 0.052 | 0.05 |
| | | 25 C. | 0.006 | 0.038 |

Following a procedure essentially as described above, oxidation of PS-80 was most pronounced in the 2.25 mL control groups at 25° C. at 3 and 6 months (Table 7). Oxidation of PS-80 was confirmed by mass spectrometry (data not shown).

In a similar study, formulations are prepared as indicated in FIG. 1. DS is dialyzed into the respective matrix and PS-80 is added or diluted to achieve the indicated final concentration. Respective formulations are filled into glass prefilled syringes and stored in chambers at room temperature, 5° C., 25° C., 30° C., or 40° C. The concentration of PS-80 is determined at the beginning of the study at room temperature, after 1, 2, or 3 months at 5° C., 25° C., or 30° C., and at 6 months at 5° C. or 25° C. The results are shown in FIG. 1.

Following a procedure as essentially described above, oxidation of PS-80 was observed in formulations comprising 5 mg/mL antibody. These data show that antibody at a concentration greater than 5 mg/mL prevents oxidation of PS-80.

Dose Ranging Clinical Trial for Migraine

A phase IIb, randomized, double-blind, placebo-controlled, dose-ranging study was conducted with 410 patients aged 18-65 years with 4 to 14 migraine headache days and at least 2 migraine attacks per month. The patients were randomly assigned (2:1:1:1:1) to placebo or 1 of 4 LY2951742 dose groups. Subcutaneous injections of LY2951742 doses of 5 mg, 50 mg, 120 mg, 300 mg or placebo were given once every 28 days for 12 weeks. The primary objective was to assess whether at least one dose of LY2951742 was superior to placebo in the prevention of migraine headache. Superiority was defined as a ≥95% posterior probability of greater improvement for any LY2951742 dose compared with placebo, as measured by the mean change from baseline in the number of migraine headache days in the last 28-day period of the 12-week treatment phase.

The results showed that all 4 dose arms were numerically superior to placebo on primary outcome measures at all-time points. One dose arm (120 mg) of LY2951742 met the primary objective (p=0.004) with a significantly greater reduction compared to placebo in the number of migraine headache days in the last 28 day period of the 12 week treatment phase.

Clinical Trial for Episodic Cluster Headache

A Phase III, randomized, double blind clinical trial is being conducted with 162 patients aged 18-65 years with at least two cluster periods lasting from 7 days to 1 year (when untreated) and separated by pain-free remission periods of ≥1 month. The patients are randomly assigned to either the placebo or treatment group. Subcutaneous injections of a pharmaceutical composition comprising LY2951742 at doses of 300 mg or placebo are given once every 30 days for 8 weeks. The primary objective is to assess whether 300 mg of LY2951742 was superior to placebo in the prevention of episodic cluster headaches. The primary outcome measured is the mean change from baseline in number of weekly cluster headache attacks after treatment.

Sequences

SEQ ID NO: 1-Exemplified LCVR (of an anti-CGRP antibody of the present invention)

DIQMTQSPSSLSASVGDRVTITCRASKDISKYLNWYQQKPGKAPKLLIYYTSGYHSGVPSRFSGSGSGTDFTLTI
SSLQPEDFATYYCQQGDALPPTFGGGTKVEIK

Sequences

SEQ ID NO: 2-Exemplified HCVR (of an anti-CGRP antibody of the present invention)
QVQLVQSGAEVKKPGSSVKVSCKASGYTFGNYWMQWVRQAPGQGLEWMGAIYEGTGKTVYIQKFADRVTITADKS
TSTAYMELSSLRSEDTAVYYCARLSDYVSGFGYWGQGTTVTVSS SEQ ID NO: 3-Exemplified LC (of an anti-CGRP antibody of the present invention)
DIQMTQSPSSLSASVGDRVTITCRASKDISKYLNWYQQKPGKAPKLLIYYTSGYHSGVPSRFSGSGSGTDFTLTI
SSLQPEDFATYYCQQGDALPPTFGGGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC SEQ ID NO: 4-Exemplified HC (of an anti-CGRP antibody of the present invention)
QVQLVQSGAEVKKPGSSVKVSCKASGYTFGNYWMQWVRQAPGQGLEWMGAIYEGTGKTVYIQKFADRVTITADKS
TSTAYMELSSLRSEDTAVYYCARLSDYVSGFGYWGQGTTVTVSSASTKGPSVFPLAPCSRSTSESTAALGCLVKD
YFPEPVTVSWNSGALTSGVHTFPAVLQSSGLYSLSSVVTVPSSSLGTKTYTCNVDHKPSNTKVDKRVESKYGPPC
PPCPAPEAAGGPSVFLFPPKPKDTLMISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKSLSLSLG SEQ ID NO: 5-Exemplified nucleotide sequence
(encoding a LC of an anti-CGRP antibody of the present invention)
gacatccagatgacccagtctccatcctccctgtctgcatctgtaggagacagagtcaccatcacttgccgagca
agtaaagacatactaagtatttaaactggtatcagcagaaaccagggaaagcccctaagctcctgatctattaca
catcaggatatcactcaggagtcccatcaaggacagtggcagtggatctgggacagatttcactctcaccatcag
cagtctgcaacctgaagattagcaacttactactgtcaacaaggtgatgcgcttcctccgacgttcggcggaggg
accaaggtggagatcaaacggactgtggctgcaccatctgtcacatcttcccgccatctgatgagcagttgaaat
ctggaactgcctctgagtgtgcctgctgaataacttctatcccagagaggccaaagtacagtggaaggtggataa
cgccctccaatcgggtaactcccaggagagtgtcacagagcaggacagcaaggacagcacctacagcctcagcag
caccctgacgctgagcaaagcagactacgagaaacacaaagtctacgcctgcgaagtcacccatcagggcctgag
ctcgcccgtcacaaagagcttcaacaggggagagtgc SEQ ID NO: 6-Exemplified nucleotide sequence (encoding a HC of an anti-CGRP antibody of the present invention)
caggtgcagctggtgcagtctggggctgaggtgaagaagcctggggtcctcagtgaaggtttcctgcaaggcatct
ggctacacctttggtaattactggatgcagtgggtgcgacaggcccctggacaagggcttgagtggatgggagct
atttatgagggaactggtaagactgtgtacattcagaagttcgccgacagagtcaccattaccgcggacaaatcc
acgagcacagcctacatggagctgagcagcctgagatctgaggacacggccgtgtattactgtgcgagattaagt
gattacgtctcgggataggctactggggccaaggaaccacggtcaccgtctcctcagcctccaccaagggcccat
cggtatcccgctagcgccctgctccaggagcacctccgagagcacagccgcccctgggctgcctgtcaaggacta
cttccccgaaccggtgacggtgtcgtggaactcaggcgccctgaccagcggcgtgcacaccaccggctgtccta
cagtcctcaggactctactccctcagcagcgtggtgaccgtgccctccagcagcagggcacgaagacctacacct
gcaacgtagatcacaagcccagcaacaccaaggtggacaagagagttgagtccaaatatggtcccccatgcccac
cctgcccagcacctgaggccgccggggggtaccatcagtcacctgacccccaaaacccaaggacactctcatgatc
tcccggacccctgaggtcacgtgcgtggtggtggacgtgagccaggaagaccccgaggtccagttcaactggtac
gtggatggcgtggaggtgcataatgccaagacaaagccgcgggaggagcagttcaacagcacgtaccgtgtggtc
agcgtcctcaccgtcctgcaccaggactggctgaacggcaaggagtacaagtgcaaggtctccaacaaaggcctc
ccgtcctccatcgagaaaaccatctccaaagccaaagggcagccccgagagccacaggtgtacaccctgcccca
tcccaggaggagatgaccaagaaccaggtcagcctgacctgcctggtcaaaggcttctaccccagcgacatcgcg
tggagtgggaaagcaatgggcagccggagaacaactacaagaccacgcctcccgtgctggactccgacggctcct
tcttcctctacagcaggctaaccgtggacaagagcaggtggcaggaggggaatgtcactcatgctccgtgatgca
tgaggctctgcacaaccactacacacagaagagcctctcccctgtctctgggttga SEQ ID NO: 7-Human αCGRP Peptide
ACDTATCVTHRLAGLLSRSGGVVKNNFVPTNVGSKAF

---

We claim:

1. A pharmaceutical formulation comprising an anti-CGRP antibody at a concentration of 50 mg/mL to 160 mg/mL, histidine buffer at a concentration of 5 mM to 20 mM, NaCl at a concentration of 50 mM to 200 mM, PS-80 at a concentration of 0.03% (w/v) to 0.07% (w/v), and a pH at 5.0 to 6.5, wherein the anti-CGRP antibody comprises two light chains (LC) and two heavy chains (HC), the amino acid sequence of the two light chains given by SEQ ID NO: 3 and the amino acid sequence of the two heavy chains given by SEQ ID NO: 4 and wherein the pharmaceutical formulation does not comprise any additional antioxidants.

2. The formulation of claim 1, wherein the concentration of anti-CGRP antibody is 50 mg/mL to 150 mg/mL.

3. The formulation of claim 1, wherein the concentration of anti-CGRP antibody is 100 mg/mL to 160 mg/mL.

4. The formulation of claim 1, wherein the concentration of anti-CGRP antibody is selected from the group consisting of 50 mg/mL, 100 mg/mL, 120 mg/mL, and 150 mg/mL.

5. The formulation of claim 1, wherein the concentration of anti-CGRP antibody is 50 mg/mL.

6. The formulation of claim 1, wherein the concentration of anti-CGRP antibody is 100 mg/mL.

7. The formulation of claim 1, wherein the concentration of anti-CGRP antibody is 120 mg/mL.

8. The formulation of claim 1, wherein the concentration of anti-CGRP antibody is 150 mg/mL.

9. The formulation of claim 1, wherein the concentration of histidine buffer is 10 mM to 15 mM.

10. The formulation of claim 9, wherein the concentration of histidine buffer is 10 mM.

11. The formulation of claim 1, wherein the concentration of NaCl is 125 mM to 175 mM.

12. The formulation of claim 11, wherein the concentration of NaCl is 150 mM.

13. The formulation of claim 1, wherein the concentration of PS-80 is 0.05% (w/v).

14. The formulation of claim 1, wherein the pH is 5.8.

15. The formulation of claim 1, wherein the concentration of anti-CGRP antibody is selected from the group consisting of 50 mg/mL, 100 mg/mL, 120 mg/mL, and 150 mg/mL, the concentration of histidine buffer is 10 mM, the concentration of NaCl is 150 mM, and the concentration of PS-80 is 0.05%, the pharmaceutical formulation having a pH between 5.5 to 6.0.

16. The formulation of claim 15, wherein the concentration of anti-CGRP antibody is 100 mg/mL.

17. The formulation of claim 15, wherein the concentration of anti-CGRP antibody is 120 mg/mL.

18. The formulation of claim 15, wherein the concentration of anti-CGRP antibody is 150 mg/mL.

19. The pharmaceutical formulation according to claim 1, wherein the formulation is suitable for subcutaneous injection.

20. The pharmaceutical formulation according to claim 19, wherein the formulation is suitable for subcutaneous injection when the formulation is stored in a prefilled syringe.

21. A pharmaceutical formulation comprising an anti-CGRP antibody at a concentration of 100 mg/mL or 120 mg/mL, histidine buffer at a concentration of 10 mM, NaCl at a concentration of 150 mM, and PS-80 at a concentration of 0.05% (w/v), the pharmaceutical formulation having a pH between 5.0 to 6.5, wherein the anti-CGRP antibody comprises two LC and a two HC, the amino acid sequence of each LC given by SEQ ID NO: 3, and the amino acid sequence of each HC given by SEQ ID NO: 4 and wherein the pharmaceutical formulation does not comprise any additional antioxidants.

22. The pharmaceutical formulation according to claim 21, wherein the pharmaceutical formulation has a pH of 5.8.

23. The pharmaceutical formulation according to claim 21, wherein the PS-80 is stable at 25° C. for at least six months.

24. The pharmaceutical formulation according to claim 21, wherein the PS-80 is stable at 5° C. for at least two years.

25. The pharmaceutical formulation according to claim 23, wherein particle formation is significantly reduced as determined by high accuracy particle counting (HIAC).

26. The pharmaceutical formulation according to claim 24, wherein particle formation is significantly reduced as determined by high accuracy particle counting (HIAC).

27. The pharmaceutical formulation according to claim 15, wherein the PS-80 is stable at 25° C. for at least six months.

28. The pharmaceutical formulation according to claim 15, wherein the PS-80 is stable at 5° C. for at least two years.

29. The pharmaceutical formulation according to claim 27, wherein particle formation is significantly reduced as determined by high accuracy particle counting (HIAC).

30. The pharmaceutical formulation according to claim 28, wherein particle formation is significantly reduced as determined by high accuracy particle counting (HIAC).

31. The pharmaceutical formulation according to claim 21, wherein the formulation is suitable for subcutaneous injection.

32. The pharmaceutical formulation according to claim 31, wherein the formulation is suitable for subcutaneous injection when the formulation is stored in a prefilled syringe.

\* \* \* \* \*

SEQUENCE LISTING

<160> NUMBER OF SEQ ID NOS: 7

<210> SEQ ID NO 1
<211> LENGTH: 107
<212> TYPE: PRT
<213> ORGANISM: Artificial Sequence
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
         35                  40                  45

Tyr Tyr Thr Ser Gly Tyr His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Ala Leu Pro Pro
                 85                  90                  95

Thr Phe Gly Gly Gly Thr Lys Val Glu Ile Lys
                100                 105

<210> SEQ ID NO 2
<211> LENGTH: 119
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Gly Asn Tyr
             20                  25                  30

Trp Met Gln Trp Val Arg Gln Ala Pro Gly Gln Gly Leu Glu Trp Met
         35                  40                  45

Gly Ala Ile Tyr Glu Gly Thr Gly Lys Thr Val Tyr Ile Gln Lys Phe
     50                  55                  60

Ala Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Asp Tyr Val Ser Gly Phe Gly Tyr Trp Gly Gln Gly
                100                 105                 110

Thr Thr Val Thr Val Ser Ser
        115

<210> SEQ ID NO 3
<211> LENGTH: 214
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
 1               5                  10                  15

Asp Arg Val Thr Ile Thr Cys Arg Ala Ser Lys Asp Ile Ser Lys Tyr
             20                  25                  30

Leu Asn Trp Tyr Gln Gln Lys Pro Gly Lys Ala Pro Lys Leu Leu Ile
         35                  40                  45

Tyr Tyr Thr Ser Gly Tyr His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Ala Leu Pro Pro
                 85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 445
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240
```

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 5
<211> LENGTH: 642
<212> TYPE: DNA
<213> ORGANISM: Artificial Sequence
<220> FEATURE:
<223> OTHER INFORMATION: Synthetic Construct

<400> SEQUENCE: 5
gacatccaga tgacccagtc tccatcctcc ctgtctgcat ctgtaggaga cagagtcacc      60
atcacttgcc gagcaagtaa agacatttct aagtatttaa actggtatca gcagaaacca     120
gggaaagccc ctaagctcct gatctattac acatcaggat atcactcagg agtcccatca     180
aggttcagtg gcagtggatc tgggacagat ttcactctca ccatcagcag tctgcaacct     240
gaagattttg caacttacta ctgtcaacaa ggtgatgcgc ttcctccgac gttcggcgga     300
gggaccaagg tggagatcaa acggactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gc                        642

<210> SEQ ID NO 6
<211> LENGTH: 1338
<212> TYPE: DNA
<213> ORGANISM: Artificial Sequence
<220> FEATURE:
<223> OTHER INFORMATION: Synthetic Construct

```
<400> SEQUENCE: 6
caggtgcagc tggtgcagtc tggggctgag gtgaagaagc ctgggtcctc agtgaaggtt      60
tcctgcaagg catctggcta cacctttggt aattactgga tgcagtgggt gcgacaggcc     120
cctggacaag gcttgagtg gatgggagct atttatgagg aactggtaa gactgtgtac      180 attcagaagt tcgccgacag agtcaccatt accgcggaca atccacgag cacagcctac     240 atggagctga gcagcctgag atctgaggac acggccgtgt attactgtgc gagattaagt     300
gattacgtct cgggatttgg ctactggggc caaggaacca cggtcaccgt ctcctcagcc     360
tccaccaagg gcccatcggt cttccccgcta gcgccctgct ccaggagcac ctccgagagc     420
acagccgccc tgggctgcct ggtcaaggac tacttcccg aaccggtgac ggtgtcgtgg      480
aactcaggcg ccctgaccag cggcgtgcac accttccgg ctgtcctaca gtcctcagga      540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc ctgcccagca cctgaggccg ccggggacc atcagtcttc      720 ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gaaagcaatg ggcagccgga gaacaactac aagaccacgc ctcccgtgct ggactccgac    1200
ggctccttct cctctacag caggctaacc gtggacaaga gcaggtggca ggaggggaat    1260
gtcttctcat gctccgtgat gcatgaggct ctgcacaacc actacacaca gaagagcctc    1320
tccctgtctc tgggttga                                                  1338
```

<210> SEQ ID NO 7
<211> LENGTH: 37
<212> TYPE: PRT
<213> ORGANISM: Homo sapiens

<400> SEQUENCE: 7

```
Ala Cys Asp Thr Ala Thr Cys Val Thr His Arg Leu Ala Gly Leu Leu
 1               5                   10                  15

Ser Arg Ser Gly Gly Val Val Lys Asn Asn Phe Val Pro Thr Asn Val
            20                  25                  30

Gly Ser Lys Ala Phe
        35
```